United States Patent [19]

Kritzer

[11] 4,054,134

[45] Oct. 18, 1977

[54] RESPIRATORS

[76] Inventor: Richard W. Kritzer, 5800 N. Pulaski Road, Chicago, Ill. 60646

[21] Appl. No.: 613,176

[22] Filed: Sept. 15, 1975

[51] Int. Cl.² .................. A61M 15/06; A62B 7/00
[52] U.S. Cl. .................. 128/208; 128/145.5; 46/180; 84/377; 272/99
[58] Field of Search ............ 128/208, 206, 147, 145.5, 128/145 R, 145.8, 146, 185, 199, 201; 46/180, 181; 84/375, 377, 378, 380 R; 116/137, 140; 272/99

[56] References Cited

U.S. PATENT DOCUMENTS

| | | | |
|---|---|---|---|
| 742,680 | 10/1903 | Kuhlemeier | 46/180 |
| 797,232 | 8/1905 | Schwarz | 84/377 X |
| 827,819 | 8/1906 | Reynolds | 46/180 |
| 2,179,993 | 11/1939 | Davies | 84/377 |
| 2,459,184 | 1/1949 | Ruffino | 84/377 |
| 2,918,917 | 12/1959 | Emerson | 128/145.6 |
| 3,006,337 | 10/1961 | Aguado | 128/145.5 |
| 3,075,317 | 1/1963 | Craft | 46/180 |
| 3,212,215 | 10/1965 | Freimauer | 46/180 |
| 3,291,127 | 12/1966 | Eimer et al. | 46/180 |
| 3,426,477 | 2/1969 | Novaco | 46/180 |
| 3,772,823 | 11/1973 | Herter | 46/180 |
| 3,837,341 | 9/1974 | Bell | 128/208 |

Primary Examiner—J. Reed Fisher
Attorney, Agent, or Firm—Emrich, Root, O'Keeffe & Lee

[57] ABSTRACT

A respirator through which a person may breath, and which vibrates the air during inhalation and exhalation in such a manner as to vibrate the cilia in the lungs of the person breathing through the respirator.

3 Claims, 8 Drawing Figures

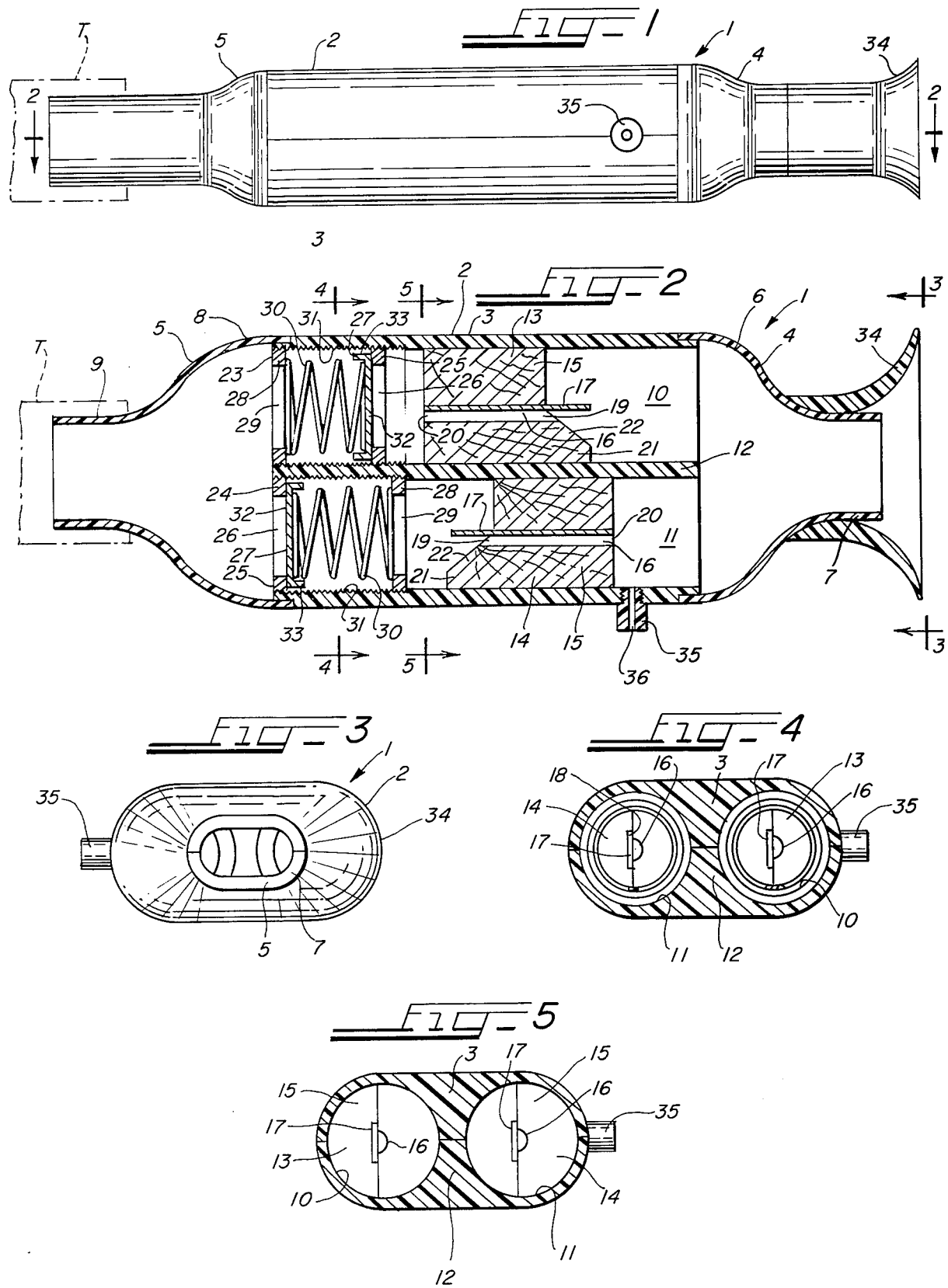

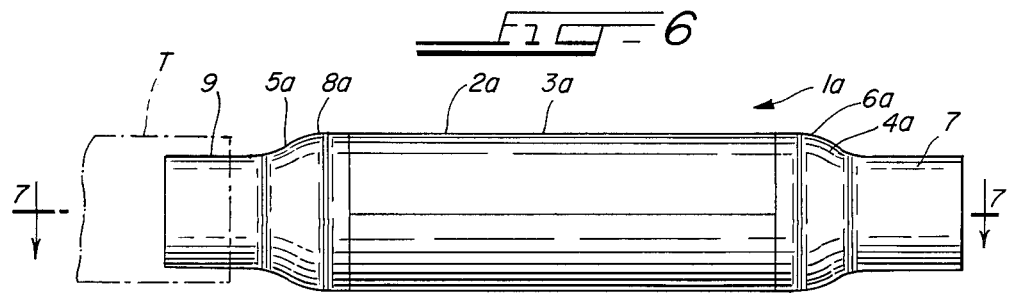
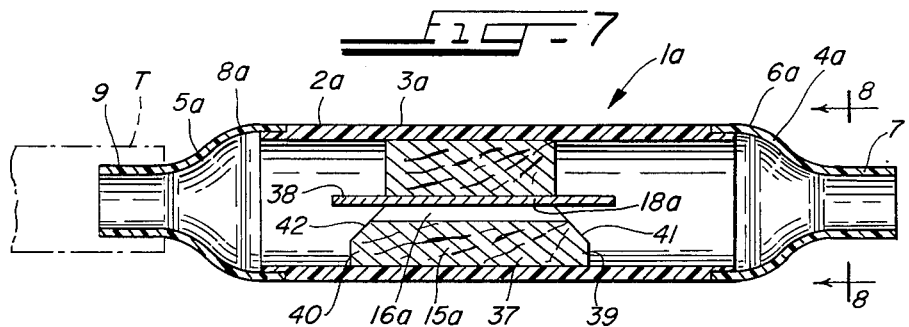
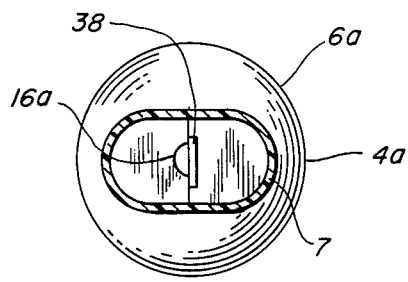

RESPIRATORS

BACKGROUND OF THE INVENTION

This invention relates to respirators, and, more particularly, to respirators that are particularly well adapted for use by persons suffering from emphysema, and the like.

It is a primary object of the present invention to afford a novel respirator.

Another object of the present invention is to afford a novel respirator which is effective to vibrate the air passing therethrough in such a manner that it is effective to vibrate the cilia in the lungs of the person breathing through the respirator.

A further object is to afford a novel respirator that is effective to so vibrate the air both on inhalation and exhalation.

Many persons suffer from ailments, such as, for example, emphysema, or the like, wherein the cilia in the lungs have become flattened down or clogged with mucous, or the like. It is my opinion, which seems to have been borne out by experimentation, that vibration of air passing into and out of the lungs of the persons suffering from the afore-mentioned conditions is effective to cause cilia, which have been flattened down, to be vibrated into an upstanding position, and to cause cilia which have been clogged with mucous, to be at least partially unclogged.

Insofar as is known, no one, prior to my invention, has afforded a respirator, or the like, through which a person can inhale and exhale, and which is effective, during such inhalation and exhalation to vibrate the air passing into and out of the persons lungs. It is an important object of the present invention, to overcome this shortcoming, and to afford a novel respirator which is effective to vibrate the cilia in the lungs of a person breathing through the respirator.

Certain articles, of course, heretofore known in the art, such as, for example, musical instruments; "Bronx cheer" toys, such as the toy shown in U.S. Pat. No. 628,870; and duck calls or goose calls, such as the goose call shown in U.S. Pat. No. 2,730,836, have caused air blown through the article to vibrate, thus causing sound to be emitted from the article. However, insofar as is known this has not, heretofore, been true with respect to, or a purpose of a respirator.

Another object of the present invention is to afford a novel respirator wherein the force required to cause air to pass therethrough during inhalation and exhalation may be quickly and easily adjusted.

Yet another object of the present invention is to afford a novel respirator wherein an auxilary fluid, such as, for example, oxygen or a medicant spray or gas, or the like, may be fed into the respirator for breathing into the lungs of the person using the respirator.

A further object of the present invention is to afford a novel respirator of the aforementioned type, which may be afforded in a convenient, relatively small, compact size, so that it may be conveniently carried and used by a person.

Another object of the present invention is afford a novel respirator of the aforementioned type, which is well adapted for use in mouth-to-mouth resuscitation of a person.

Another object of the present invention is to afford a novel respirator of the aforementioned type, which is practical and efficient in operation, and which may be readily and economically produced commercially.

Other and further objects of the present invention will be apparent from the following description and claims and are illustrated in the accompanying drawings which, by way of illustration, show the preferred embodiments of the present invention and the principles thereof and what I now consider to be the best mode in which I have contemplated applying these principles. Other embodiments of the invention embodying the same or equivelent principles may be used and structural changes may be made as desired by those skilled in the art without departing from the present invention and the purview of the appended claims.

SUMMARY OF THE INVENTION

A respirator which is particularly well adapted for use by persons suffering from emphysema, or the like, and which embodies a housing having a mouthpiece at one end thereof, which a person may inhale and exhale, vibrator mechanism being mounted in the housing in such position, that, as a person inhales and exhales through the mouthpiece, and therefore, the respirator, the air or other gas passing through the respirator is caused to vibrate in such a manner as to cause the air, and, therefore, the cilia in the lungs of the person breathing through the respirator to vibrate.

DESCRIPTION OF THE DRAWING

In the drawings:

FIG. 1 is a side elevational view of a respirator embodying the principles of the present invention;

FIG. 2 is a longitudinal sectional view taken substantially along the line 2—2 in FIG. 1;

FIG. 3 is an end view of the respirator shown in FIG. 1, looking in the direction of the arrows 3—3 in FIG. 2;

FIG. 4 is a detail sectional view taken substantially along the line 4—4 in FIG. 2;

FIG. 5 is a detail sectional view taken substantially along the line 5—5 in FIG. 2;

FIG. 6 is a side elevational view, similar to FIG. 1, but showing a modified form of the present invention;

FIG. 7 is a longitudinal sectional view taken substantially along the line 7—7 in FIG. 6; and FIG. 8 is a detail cross-sectional view taken substantially along the line 8—8 in FIG. 7.

DESCRIPTION OF THE EMBODIMENTS SHOWN HEREIN

A respirator or breathing unit 1 is shown in FIGS. 1-5, inclusive, of the drawings, to illustrate the presently preferred embodiment of the present invention.

The respirator 1 embodies an elongated, tubular housing, which is substantially eliptical-shaped in transverse cross section. The housing 2 embodies an elongated, tubular body portion 3 and two end portions or end caps 4 and 5 mounted on respective opposite ends of the body portion 3, FIGS. 1 and 2. The end cap 4 embodies an inner end portion 6, mounted on one end of the body portion 3 in surrounding relation thereto, FIG. 2, and an outer end portion 7, which is smaller in cross sectional size then the inner end portion 6, and affords a mouth piece for a purpose which will be discussed in greater detail presently. The end cap 5 is identical in construction to the end cap 4, and embodies an inner end portion 8 mounted on the other end of the body portion 3, and an outer end portion 9, which is smaller than the inner end portion 8, and affords a coupling member for a purpose which will be discussed in greater detail presently.

The body portion 3 has two passageways 10 and 11 extending longitudinally therethrough in parallel relation to each other. The passageways 10 and 11 are separated from each other throughout their length by a partition wall 12, FIGS. 2 and 4, and each is preferably round in transverse cross section, FIGS. 4 and 5. Two vibrators 13 and 14 are mounted in the passageways 10 and 11, respectively. The vibrators 13 and 14 are identical in construction, and each embodies an elongated body portion 15, having a passageway 16 extending longitudinally therethrough. The passageway 16 in each of the vibrators 13 and 14 is substantially semi-circular in transverse cross section, FIGS. 4 and 5, and an elongated reed 17, which is substantially rectangular in transverse cross section is mounted at one side of each of the passageways 16 in a channel 18, which extends longitudinally through the respective body portion 15 in adjacent relation to the passageway 16. Each of the reeds 17 preferably is disposed in the respective channels 18 with a force fit, and, if desired, may be further secured to the body portion, 15, in which it is mounted, by suitable means, such as, for example, an adhesive, not shown.

Each of the passageways 16 has an inlet end 19 and an outlet end 20, and each of the body portions 15 has a tongue 21 which projects outwardly beyond the inlet end 19 of the adjacent passageway 16 on the side thereof remote from the reed 17, the face 22 of the tongue 21, which faces toward the reed 17, sloping outwardly away from the adjacent passageway 16 at an acute angle to the longitudinal axis of the latter.

It is to be observed that although the vibrators 13 and 14 are identical in construction, they are mounted in the respective passageways 10 and 11 in reverse direction relative to each other, the vibrator 13 being disposed in the passageway 10 in such position that the reed 17 thereof projects outwardly away from the body portion 15 toward the cap 5, and the vibrator 14 being mounted in the passageway 11 in such position that the reed 17 thereof projects outwardly from the body portion 15 thereof toward the cap 4.

With the vibrators 13 and 14 constructed in the aforementioned manner and mounted in the respective passageways 10 and 11, air passing through the vibrators 13 and 14 from the inlet end 19 to the outlet end 20 of the respective passageways 16 will cause the reeds 17 to be rapidly vibrated and thus cause vibrations to occur in the air in the respirator 1, and in the air in the trachea and lungs of the person breathing through the respirator 1. Preferably, the vibrations thus caused to occur in the air passing through the respirator 1 are at such a frequency as to cause sound, which is audible to the human ear to emanate from the respirator 1, for reasons which will be discussed in greater detail hereinafter.

The respirator 1 also embodies two one-way valves 23 and 24 mounted in the passageways 10 and 11, respectively. Each of the valves 23 and 24 is identical in construction, and each embodies an annular seat 25 having a central opening 26 extending therethrough; a valve member 27 movable into and out of engagement with the respective seat 25; an annular retainer 28, having a central opening 29 extending therethrough; and a compression coil spring 30 disposed between the valve member 27 and the seat 25 in position to yieldingly normally hold the valve member 27 in engagement with the seat 25. The interiors of the passageways 10 and 11, remote from the mouthpiece 7 have internal threads 31 formed therein. The outer peripheries of the seats 25 and the retainers 28 are threaded, and in the assembled respirator 1, the seats 25 and the retainers 28 of the valves 23 and 24 are threadly engaged with, and held by the internal threads 31 in the passageways 10 and 11, respectively.

Each of the valve members 27 has a round, substantially flat body portion 32, from one side of the outer periphery of which projects an annular flange 33, FIG. 2. The valve members 27 are of such size that, when the faces of the body portions 32 thereof remote from the flanges 33 are disposed in abutting engagement with the respective seats 25, the valve members 27 are effective to close the openings 26 through the latter.

In the assembled valves 23 and 24, the retainers 28 and the seats 25 are disposed in spaced relation to each other, with the valve members 27 disposed therebetween in position wherein the flanges 33 project toward the retainers 28, FIG. 2. The springs 30 are disposed between, and are abuttingly engaged with the retainers 28 and the valve members 27 of the respective valves 23 and 24, and are of such size that they fit into the concavity defined by the flanges 33 on the respective valves 27, FIG. 2.

The valve members 23 and 24, which it will be remembered are identical in construction, are disposed in reverse relation to each other in the passageways 10 and 11, respectively. Thus, the valve member 23 is disposed in the passageway 10 in position wherein the outer face of the seat 25 thereof faces toward the mouth piece 7; and the valve member 24 is disposed in the passageway 11 in such position that the outer face of the seat 25 thereof faces toward the coupling member 9. Thus, when a person is breathing through the mouthpiece 7 of the cap 5, he may exhale through the passageway 10 and inhale through the passageway 11, the valves 23 and 24 being effective to prevent inhalation through the passageway 8 and exhalation through the passageway 9. With this construction, the vibrator 13 may be caused to vibrate during exhalation through the respirator 1, and the vibrator 14 may be caused to vibrate during inhalation through the respirator 1.

With the seats 25 and retainers 28 of the valves 23 and 24 threadly mounted in the respective passageways 10 and 11, the seats 25 and the retainers 28 of the respective valves 23 and 24 may be readily adjusted toward and away from each other by rotating the same, to thereby adjust the force with which the respective springs 30 urge the valve members 27 engages thereby against the adjacent seats 25. Such adjustment is effective to regulate the force with which a person must exhale and inhale through the respirator 1 in order to open the valves 23 and 24, respectively, and thereby cause air to flow through the passageways 10 and 11, respectively, during such exhalation and inhalation.

In the preferred form of the invention shown in FIGS. 1–5, a face piece 34, which is of a type well known in the respirator art, is mounted on the mouthpiece 7 on the cap 5 in surrounding relation thereto. The face piece 34 may be made of any suitable, soft, plyable material, such as, for example, sponge rubber, and projects and flares outwardly from the cap 5. The face piece 34 is so disposed on the mouth piece 7 of the cap 5, that when the mouthpiece 7 is disposed in operative position in a person's mouth, the face piece 34 is pressed against the face of the person in sealing engagement therewith so as to assist in insuring against leakage between the respirator 1 and the mouth of the person breathing therethrough. Preferably, the mouth piece 7 is substantially eliptical in cross sectional shape, as shown in FIG. 3, so as to lend itself to ready sealing engagement by the lips of the person in whose mouth it is disposed.

It will be remembered that, in the preferred form of the invention shown in FIGS. 1–5, the outer end portion 9 of the cap 5 is identical in construction to the mouthpiece 7 of the cap 4. With this construction, the caps 4 and 5 are interchangeable for manufacturing purposes. Also, with the coupling member 9 afforded on the cap 5, the respirator 1, if desired, may be readily connected to a suitable source of gas, such as, for example, oxygen or the like, by attaching a tube, such as the tube T, shown in broken lines in FIGS. 1 and 2, extending from the source of gas, not shown, to the coupling member 9 on the cap 5, the flow of oxygen, or other gas, through the respirator 1, if at the proper rate, causing the vibrator 14 to vibrate in the same manner as if the person using the respirator 1 were inhaling.

In addition, with the end portion 9 being afforded on the cap 5, it affords a mouthpiece which is identical to the mouthpiece 7 at the other end of the respirator 1. With this construction a novel respirator is afforded for use in mouth-to-mouth resuscitation. In such use, the mouthpiece 7 may be placed in a patient's mouth, with the face piece 34 manually held in engagement with the patient's face, and the person performing the resuscitation efforts may alternately blow into the end portion 9 and press on the patient's chest to thereby cause the patient to "inhale" and "exhale", respectively. Preferably, such "inhaling" and "exhaling" is effective to cause the aforementioned desired vibration of the vibrators 14 and 13, respectively to thereby cause corresponding vibration of the air in the trachea and lungs of the person being resuscitated.

Also, in the preferred form of the invention shown in FIGS. 1–5, a coupling member 35 having a passageway 36 extending therethrough, FIG. 2, is mounted in and extends through the sidewall of the body portion 3 of the housing 2 between the vibrator 14 and the cap 4, If desired, auxillary material, such as, for example, a medicant spray or gas may be fed through the passageway 36 into the passageway 11 while a person is using the respirator 1, so that the auxillary material mixes with the main material, such as, for example, the aforementioned air or oxygen passing into the respirator 1 through the cap 4, and is inhaled with the main material into the lungs of the person using the respirator 1.

The reeds 17 of the vibrators 13 and 14 may be made of any suitable material, but, preferably, are made of a suitable composition material, such as, for example, a composition of hard rubber, or a suitable plastic material, such as, for example, polystyrene. Similarly, the body portions 15 of the valves 13 and 14 may be made of any suitable material, but, preferably, are made of a suitable, relatively hard wood, such as, for example, mahogony, or the like.

Also, the housing 2 of the respirator 1 may be made of any suitable material, but, preferably, is made of a suitable plastic material, such as, for example, polypropylene, polyehtylene or polystyrene. In addition, the valves 23 and 24 may be made of any suitable material, but preferably, are made from a suitable metal, such as, for example, steel, or the like.

It will be remembered that, preferably, the respirator 1 is so constructed that the vibrations of the reeds 16 in the vibrators 13 and 14, during exhalation and inhalation, respectively, through the respirator 1 are effective to cause a sound to emanate from the respirator 1 which is audible to the human ear. One reason that this is preferred is that it affords a means for monitoring the proper operation of the respirator 1, not only by the person who is breathing through the respirator 1, but also by another person, such as an attendant or nurse, the person monitoring the same being able to determine whether vibrations are being set up during inhalation and exhalation through the respirator 1 by the presence or absence of sound emanating therefrom. Another reason that I prefer that vibrations emanating from the respirator 1 be of a frequency audible to the human ear is that vibrations in the frequencies audible to the human ear appear to cause vibrations of the air in the lungs of a person breathing through the respirator 1 which are most effective in beneficially vibrating the cilia in the lungs of the person using the respirator. This is particularly true in the lower ranges of the frequencies audible to the human ear, and, as a result, I prefer that the vibrators 13 and 14 be such that the vibrations caused by the inhalation and exhalation of a person using my novel respirator 1 be not substantially less than 100 vibrations per second and not substantially more than 300 vibrations per second.

A modified form of the present invention is illustrated in FIGS. 6–8, inclusive, of the drawings. This modified form of the invention embodies the same general principles as the preferred form illustrated in FIGS. 1–5, inclusive, and parts which are the same as parts shown in FIGS. 1–5 are indicated by the same reference nuerals, and parts which are similar but which have been substituted for parts shown in FIGS. 1–5 are indicated by the same reference numerals with the suffix "a" added.

The respirator 1a embodies an elongated, tubular housing 2a, which, like the housing 2 in the respirator 1 embodies an elongated body member 3a having end pieces or caps 4a and 5a mounted on the opposite ends thereof, FIGS. 6 and 7. However, unlike the body portion 3 of the housing 2, the body portion 3a of the housing 2a is substantially circular in transverse cross section. The inner end portions 6a of the cap 4a is complementary in transverse cross sectional shape to the body portion 3a and, the outer end portion of the cap 4a affords a mouthpiece 7, which is substantially eliptical-shaped in transverse cross section. The cap 5a is identical in construction to the cap 4a, and the inner end portion 8a thereof is mounted on the end of the housing 3a remote from the cap 4a. The cap 5a terminates at its outer end portion in a connecting member 9.

An elongated vibrator 37 is mounted in the body portion 3a of the housing 2a midway between the caps 4a and 5a, FIG. 7. Like the vibrators 13 and 14, the vibrator 37 embodies an elongated body portion 15a, which may be made of any suitable material, such as, for example, the afore-mentioned mahogany, or the like. Like the body portions 15, the body portion 15a has an elongated passageway 16a, which is substantially semi-circular in transverse cross section, and an elongated channel 18a, which is substantially rectangular in transverse cross section, extending axially therethrough in side-by-side relation to each other. An elongated reed 38 is mounted in the channel 18a. However, unlike the reeds 17 in the vibrators 13 and 14, the reed 38 projects outwardly from both ends of the body portion 15a of the vibrator 37. Also, unlike the body portions 15 of the vibrators 13 and 14, the body portion 15a of the vibrator 37 has two tongues 39 and 40 projecting outwardly beyond respective ends of the passageways 16a, FIG. 7, each of the tongues 39 and 40 having upper faces 41 and 42, respectively, thereon which are disposed at an acute angle to the horizontal, as viewed in FIG. 7, in facing relation to respective outwardly projecting end portions of the reed 38.

The various parts of the housing 2a and the vibrator 37 may be made of any suitable material, but, preferably, are made from the same materials as previously discussed with respect to the housing 2 and the vibrators 13 and 14.

With the respirator 1a constructed in the afore-mentioned manner, when a person places the mouthpiece 7 thereof in his mouth and breathes through the respirator 1a, exhalation through the respirator 1a causes the end portion of the reed 38, which projects toward the mouthpiece 7 to be rapidly vibrated, but is ineffective to cause the other end portion of the reed 38 to be vibrated; and inhalation through the respirator 1a is effective to cause the end portion of the reed 38, which projects toward the coupling member 9 to be rapidly vibrated, but is ineffective to cause vibration of the end portion of the reed 38 projecting toward the mouthpiece 7. Thus, during inhalation and exhalation through the respirator 1a, by a person holding the mouthpiece 7 in his mouth, the left and right end portion, respectively, of the reed 38, as viewed in FIG. 7, are caused to rapidly vibrate, and thus cause vibrations to occur in the air in the respirator 1a, and in the air in the trachea and lungs of the person breathing through the respirator 1a. Preferably, the vibrator 37 is of such construction that the frequency of the aforementioned vibrations of the reed 38 is the same as that discussed with respect to the frequency of vibration of the reeds 17 of the vibrators 13 and 14.

It is to be observed that the respirator 1a shown in FIGS. 1–8 does not embody a face piece, such as the face piece 34 embodied in the respirator 1, shown in FIGS. 1–5. However, as will be appreciated by those skilled in the art, if desired, a face piece, such as the face piece 34 may be mounted on the mouth piece 7 of the respirator 1a in the same manner that the face piece 34 is mounted on the mouthpiece 7 of the respirator 1.

From the foregoing, it will be seen that the present invention affords a novel respirator which is effective, in a novel and expeditious manner, to vibrate air passing therethrough, as well as air in communication with the latter air, such as, for example, the air in the trachea and lungs of a person breathing through the respirator.

In addition, it will be seen that the present invention affords a novel respirator wherein the air passing therethrough, and the aforementioned air in communication therewith, is caused to so vibrate during both inhalation and exhalation through the respirator.

Also, it will be seen that the present invention affords a novel respirator which affords a novel, device for vibrating the cilia in the lungs of a patient using the same.

In addition, it will be seen that the present invention affords a novel respirator of the aforementioned type, which is practical and efficient in operation, and which may be readily and economically produced commercially.

Thus, while I have illustrated and described the preferred embodiments of my invention, it is to be understood that these are capable of variation and modification, and I therefore do not wish to be limited to the precise details set forth, but desire to avail myself of such changes and alterations as fall within the purview of the following claims.

I claim:
1. A respirator comprising
   a. an elongated tubular housing having a mouthpiece at one end thereof for insertion into a person's mouth to thereby enable the person to
      1. inhale in one direction longitudinally through said housing, and
      2. exhale longitudinally through said housing in the direction opposite to said one direction, and
   b. means in said housing for vibrating material inhaled and exhaled therethrough,
   c. said housing having two passageways extending longitudinally through at least a portion thereof in side-by-side relation to each other,
   d. said means for vibrating material inhaled through said housing comprising means mounted in one of said passageways,
   e. said means for vibrating material exhaled through said housing comprising means mounted in the other of said passageways,
   f. each of said passageways having
      1. an annular valve seat mounted therein for the passage of such material therethrough,
      2. a valve member mounted therein in position to be moved into and out of closing engagement with said valve seat,
      3. spring means mounted therein and yieldingly engaged with said valve member for yieldingly holding said valve member in said closing engagement with said valve seat, and
      4. a retainer member mounted therein and engaged with said spring means on the side thereof remote from said valve member in position to hold said spring means in engagement with said valve member,
   g. said valve seats being threaded into respective ones of said passageways and being adjustable longitudinally thereof,
   h. said retainer members being threaded into respective ones of said passageways and being adjustable longitudinally thereof,
   i. said valve member in said one passageway being disposed in said closing engagement during such exhalation through said housing, and
   j. said valve member in said other passsageway being disposed in said closing engagement during such inhalation through said housing.

2. A respirator for a person suffering from emphysema, or the like, for causing vibration of air in the person's lungs, comprising
   a. an elongated tubular housing having a mouthpiece at one end thereof for insertion into a person's mouth to thereby enable the person to
      1. inhale in one direction longitudinally through said housing, and
      2. exhale longitudinally through said housing in the direction opposite to said one direction,
   b. said mouthpiece having an unobstructed, continuous outer peripheral surface of such size as to be completely surroundingly engaged by the lips of such a person during such inhalation and exhalation therethrough,
   c. means in said housing for vibrating material inhaled and exhaled therethrough, d. valve means for limiting inhalation and exhalation through said housing,
e. said housing having two separated passageways extending longitudinally through at least a portion thereof,
f. said means for vibrating material inhaled through said housing comprising means mounted in one of said passageways,
g. said means for vibrating material exhaled through said housing comprising means mounted in the other of said passageways,
h. said valve means comprising 1. a one-way valve mounted in said one passageway for permitting inhalation and preventing exhalation therethrough, and
  2. another one-way valve mounted in said other of said passageways for permitting exhalation and preventing inhalation therethrough, and
i. means disposed on said housing between said first mentioned means and said mouthpiece for feeding auxiliary material into said housing for inhalation through said mouthpiece.

3. A respirator as defined in claim 2, and in which
a. said first mentioned means vibrates said air passing through said housing at a frequency not substantially less than 100 vibrations per second and not substantially more than 300 vibrations per second.

* * * * *